US00PP35057P2

(12) United States Plant Patent
Beers

(10) Patent No.: US PP35,057 P2
(45) Date of Patent: Mar. 21, 2023

(54) ***GERBERA* PLANT NAMED 'MAJPUR21AA'**

(50) Latin Name: *Gerbera hybrida*
Varietal Denomination: MAJPUR21AA

(71) Applicant: HilverdaFlorist B.V., De Kwakel (NL)

(72) Inventor: Martin Beers, Hoofddorp (NL)

(73) Assignee: HilverdaFlorist B.V., De Kwakel (NL)

( * ) Notice: Subject to any disclaimer, the term of this patent is extended or adjusted under 35 U.S.C. 154(b) by 0 days.

(21) Appl. No.: 17/747,755

(22) Filed: May 18, 2022

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./357
CPC ... A01H 5/02; A01H 5/00; A01H 6/14; A01H 6/1456
See application file for complete search history.

(56) References Cited

PUBLICATIONS

HilverdaFlorist Majestic Purple, retrieved on Jun. 27, 2022 at https://www.hilverdaflorist.com/assortment/product/majestic-purple/, one page. (Year: 2022).*
Knox Horticulture Young Plant Programs 2021-2022, retrieved on Jun. 27, 2022 at https://www.knoxhort.com/wp-content/uploads/Documents/KnoxHort_YP-Program-Brochure.pdf, pp. 1, 8, 56-58. (Year: 2022).*

* cited by examiner

*Primary Examiner* — June Hwu
(74) *Attorney, Agent, or Firm* — C. Anne Whealy

(57) ABSTRACT

A new and distinct cultivar of *Gerbera* plant named 'MAJPUR21AA', characterized by its broadly upright and uniformly mounding plant habit; moderately vigorous growth habit; dense and bushy appearance; numerous inflorescences with reddish purple-colored ray florets; upright and moderately strong peduncles; good garden performance and relative tolerance to low temperatures.

1 Drawing Sheet

Botanical designation: *Gerbera hybrida.*
Cultivar denomination: 'MAJPUR21AA'.

BACKGROUND OF THE INVENTION

The present invention relates to a new and distinct cultivar of *Gerbera* plant, botanically known as *Gerbera hybrida* and hereinafter referred to by the cultivar name 'MAJPUR21AA'.

The new *Gerbera* plant is a product of a planned breeding program conducted by the Inventor in De Kwakel, The Netherlands. The objective of the breeding program is to create new garden *Gerbera* plants with numerous attractive inflorescences, resistant to cold temperatures and good garden performance.

The new *Gerbera* plant originated from a cross-pollination during the spring of 2015 of a proprietary selection of *Gerbera hybrida* identified as code number 10T0518, not patented, as the female, or seed, parent with a proprietary selection of *Gerbera hybrida* identified as code number 13T10301, not patented, as the male, or pollen, parent. The new *Gerbera* plant was discovered and selected as a single flowering plant from within the progeny of the stated cross-pollination in a controlled greenhouse environment in De Kwakel, The Netherlands during the summer of 2016.

Asexual reproduction of the new *Gerbera* plant by vegetative terminal cuttings and in vitro meristem culture since the autumn of 2016 has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MAJPUR21AA'. These characteristics in combination distinguish 'MAJPUR21AA' as a new and distinct *Gerbera* plant:

1. Broadly upright and uniformly mounding plant habit.
2. Moderately vigorous growth habit.
3. Dense and bushy appearance.
4. Numerous inflorescences with reddish purple-colored ray florets.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences with larger ray florets than plants of the female parent selection.
2. Plants of the new *Gerbera* have reddish purple-colored ray florets whereas plants of the female parent selection have white-colored ray florets.

Plants of the new *Gerbera* differ primarily from plants of the male parent selection in the following characteristics:

1. Plants of the new *Gerbera* have shorter and narrower leaves than plants of the male parent selection.
2. Plants of the new *Gerbera* have lighter reddish purple-colored ray florets than plants of the male parent selection.

Plants of the new *Gerbera* can be compared to plants of the *Gerbera hybrida* 'Sweet Fiesta', not patented. In side-by-side comparisons, plants of the new *Gerbera* differ from plants of 'Sweet Fiesta' in the following characteristics:

1. Plants of the new *Gerbera* have slightly larger inflorescences than plants of 'Sweet Fiesta'.
2. Ray florets of plants of the new *Gerbera* are darker reddish purple in color than ray florets of plants of 'Sweet Fiesta'.
3. Plants of the new *Gerbera* have thicker peduncles than plants of 'Sweet Fiesta'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph is a side perspective view of a typical flowering plant of 'MAJPUR21AA' grown in a container.

DETAILED BOTANICAL DESCRIPTION

The aforementioned photograph and following observations and measurements describe plants grown during the winter and early spring in 17-cm containers in a glass-covered greenhouse in De Kwakel, The Netherlands and under cultural practices typical of commercial garden *Gerbera* production. During the production of the plants, day and night temperatures ranged from 12° C. to 15° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'MAJPUR21AA'.

Parentage:

*Female, or seed, parent*.—Proprietary selection of *Gerbera hybrida* identified as code number 10T0518, not patented.

*Male, or pollen, parent*.—Proprietary selection of *Gerbera hybrida* identified as code number 13T10301, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; broadly upright and uniformly mounding plant habit; roughly flattened globular in shape; numerous leaves arranged in basal rosettes; dense and bushy habit; inflorescences held above the foliar plane on erect and strong basal peduncles; moderately vigorous growth habit and moderate growth rate.

*Plant height, soil level to top of foliar plane*.—About 23.1 cm.

*Plant height, soil level to top of inflorescences*.—About 35.4 cm.

*Plant width or spread*.—About 46.6 cm.

Leaf description:

*Arrangement*.—Alternate, basal, simple.

*Length*.—About 16 cm.

*Width*.—About 8 cm.

*Shape*.—Ovate to elliptic.

*Apex*.—Obtuse.

*Base*.—Attenuate.

*Margin*.—Shallowly repand to shallowly angulate or entire; proximally, coarsely and irregularly angulate; sinuses shallow and parallel.

*Texture and luster, upper surface*.—Main vein, sparsely to moderately pubescent; strongly rugose; moderately glossy.

*Texture and luster, lower surface*.—Moderately to densely pubescent; slightly rugose; matte.

*Venation pattern*.—Pinnate.

*Color*.—Developing leaves, upper surface: Slightly darker than 143A. Developing leaves, lower surface: Close to 191B. Fully expanded leaves, upper surface: Close to 137A; venation, close to 144B. Fully expanded leaves, lower surface: Close to a blend of 147C and 191B; venation, close to 144C.

*Petioles*.—Length: About 8 cm. Diameter: About 3.5 mm. Texture and luster, upper and lower surfaces: Densely pubescent; slightly glossy. Strength: Moderately strong to strong. Color, upper surface: Close to N144C. Color, lower surface: Close to 150A; towards the base, close to 151A.

Inflorescence description:

*Appearance*.—Composite inflorescence form with oblanceolate-shaped ray florets; solitary semi-double inflorescences borne on upright and moderately strong peduncles and held above the foliar plane; ray and disc florets arranged acropetally on a capitulum; inflorescences face upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about two to four weeks on the plant; inflorescences persistent.

*Quantity of inflorescences*.—Freely flowering habit with about ten inflorescences per plant at one time.

*Inflorescence buds*.—Height: About 2 cm. Diameter: About 1.9 cm. Shape: Broadly oblong. Texture and luster: Densely pubescent; matte. Color: Close to 138B; immature ray florets, close to 145A and 145B.

*Inflorescence size*.—Diameter: About 7 cm. Depth (height): About 2.9 cm. Diameter of disc: About 2.1 cm.

*Receptacles*.—Height: About 4 mm. Diameter: About 5 mm. Shape: Broadly rhomboidal. Color: Close to 155A.

*Ray florets*.—Quantity and arrangement: About 160 per inflorescence; ray florets arranged in about four outer whorls and two inner whorls of smaller ray florets. Orientation: Proximally, about 30° from vertical; distally, about 60° from vertical. Outer whorls of ray florets: Length: About 3.8 cm. Width: About 6 mm. Shape: Oblanceolate. Apex: Narrowly obtuse. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to 71A; apices, close to NN155D. When opening, lower surface: Close to 70B tinged with close to N144B. Fully opened, upper surface: Close to N74A; towards the apex, close to N74B; apical margins and apices, close to 155A; venation, close to N74A and towards the apex, close to N74B; color does not change with subsequent development. Fully opened, lower surface: Close to a blend of 145C and 150D; towards the margins, close to 157A; venation, close to a blend of 145C and 150D; color does not change with subsequent development. Inner whorls of ray florets: Length: About 2.5 cm. Width: About 2 mm. Shape: Narrowly oblanceolate. Apex: Narrowly obtuse. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to 70A; apices, close to NN155D. When opening, lower surface: Close to a blend of 70B and 70C. Fully opened, upper surface: Close to 70B; apical margins and apices, close to NN155D; venation, close to 70B; color does not change with subsequent development. Fully opened, lower surface: Close to 70C; towards the margins and apex, close to NN155D; venation, close to N155B; color does not change with subsequent development.

*Disc florets*.—Quantity and arrangement: About 200 disc florets at center of the inflorescence arranged in about a six-whorl spiral. Length: About 1.4 cm. Width: About 6 mm. Shape: Tubular with one or two narrow free lobes and one broader free lobe. Apex: Acute and recurved; upper 20%, free. Base: Lower 80%, fused. Margin, free lobes: Entire; not undulate. Texture, upper surface: Smooth, glabrous; moderately velvety; matte. Texture, lower surface: Smooth, glabrous; slightly velvety; slightly glossy. Color: When opening and fully opened, inner surface: Distally, close to 70B and apex, close to NN155D; mid-section and base, close to 157D. When opening and fully opened, outer surface: Distally, close to 70C to 70D and apex, close to NN155D; mid-section and base, close to 157D.

*Pappus*.—Quantity of hairs per floret: Numerous. Length: About 6 mm. Diameter: Less than 1 mm. Texture and luster: Soft; matte. Color: Close to 162D.

*Phyllaries*.—Quantity and arrangement: About 60 per inflorescence arranged in about three whorls. Length: About 1.5 cm. Width (at base): About 2.75 mm. Shape: Linear. Apex: Narrowly acute. Base: Cuneate. Margin: Entire. Texture and luster, upper surface: Smooth, glabrous; moderately glossy. Texture and luster, lower surface: Densely pubescent; matte. Color, upper surface: Close to 143B. Color, lower surface: Close to 138A.

*Peduncles*.—Length: About 32.1 cm. Diameter: Proximally, about 4 mm; distally, about 3 mm. Strength: Moderately strong. Angle: About 15° from vertical. Texture and luster: Densely pubescent; moderately glossy. Color: Close to 144A; distally, close to 146B and proximally, close to 152D.

*Reproductive organs*.—Androecium (present on disc florets only): Quantity per floret: Five. Filament length: About 6 mm. Filament color: Close to 157D. Anther shape: Linear; basifixed. Anther size: About 3.5 mm by 0.3 mm. Anther color: Close to 13A. Pollen amount: Scarce. Pollen color: Close to 13B. Gynoecium (present on ray and disc florets): Quantity per floret: One. Pistil length: Ray florets, about 8 mm, and disc florets, about 10 mm. Stigma diameter: About 0.5 mm. Stigma shape: Cleft. Stigma color: Close to N155B. Style length: Ray florets, about 7.5 mm, and disc florets, about 9.5 mm. Style color: Close to N155B. Ovary color: Close to 155A.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −5° C. to about 35° C. and to be cold hardy to USDA Hardiness Zone 7.

It is claimed:

1. A new and distinct *Gerbera* plant named 'MAJPUR21AA' as illustrated and described.

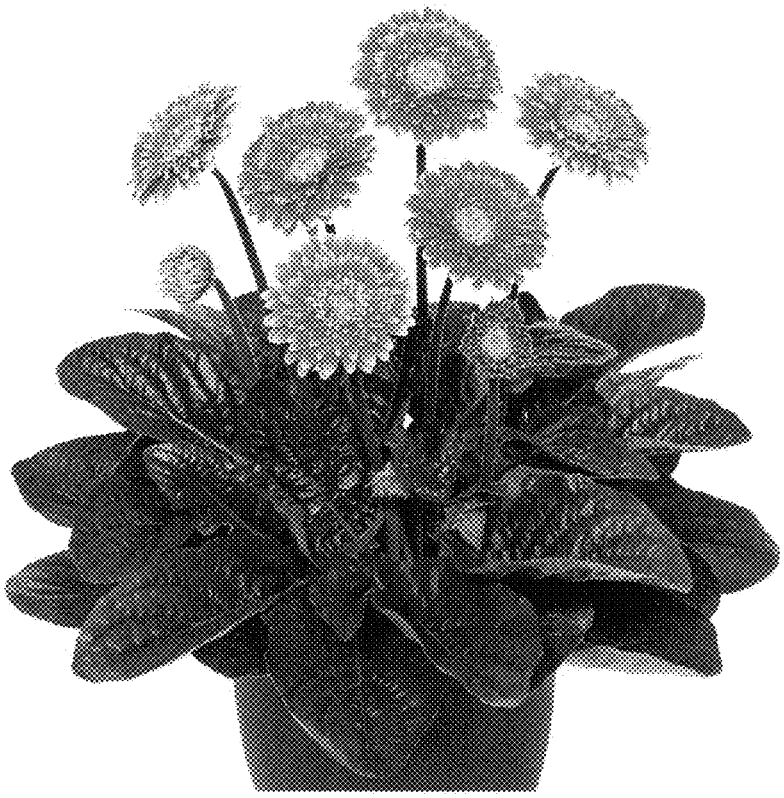

* * * * *